United States Patent
Ryan

(10) Patent No.: US 10,650,064 B2
(45) Date of Patent: May 12, 2020

(54) DIETARY REGIME FOR TREATMENT OF ACNE

(71) Applicant: RED PINNACE LIMITED, Hong Kong (CN)

(72) Inventor: Marie Helen Ryan, Vientiane (LA)

(73) Assignee: RED PINNACE LIMITED, Hong Kong (CN)

( * ) Notice: Subject to any disclaimer, the term of this patent is extended or adjusted under 35 U.S.C. 154(b) by 49 days.

(21) Appl. No.: 15/031,852

(22) PCT Filed: Oct. 27, 2014

(86) PCT No.: PCT/IB2014/002312
§ 371 (c)(1),
(2) Date: Apr. 25, 2016

(87) PCT Pub. No.: WO2015/059561
PCT Pub. Date: Apr. 30, 2015

(65) Prior Publication Data
US 2016/0278412 A1  Sep. 29, 2016

Related U.S. Application Data

(60) Provisional application No. 61/895,434, filed on Oct. 25, 2013.

(51) Int. Cl.
*A23L 33/00* (2016.01)
*G06F 16/951* (2019.01)
*A61K 45/06* (2006.01)

(52) U.S. Cl.
CPC ............ *G06F 16/951* (2019.01); *A23L 33/00* (2016.08); *A23L 33/30* (2016.08); *A61K 45/06* (2013.01); *A23V 2002/00* (2013.01)

(58) Field of Classification Search
CPC ................................. A23L 33/00; A23L 33/30
See application file for complete search history.

(56) References Cited

U.S. PATENT DOCUMENTS

2008/0059342 A1* 3/2008 Culver ............... G06F 19/3475
705/28

FOREIGN PATENT DOCUMENTS

| CN | 1228705 A | 9/1999 |
| CN | 101228901 A | 7/2008 |
| EP | 1597978 A1 | 11/2005 |
| WO | 1998/04270 A1 | 2/1998 |

OTHER PUBLICATIONS

Mercola—"The Root Cause of Acne Your Doctor Will Never Tell You About". Available online as of May 31, 2011 from https://articles.mercola.com. pp. 1-12. (Year: 2011).*
The Primal Parent: "IBS, Depression and Skin Problems in Fructose Malabsorption". Available as of Mar. 31, 2012 from http://theprimalparent.com. pp. 1-50. (Year: 2012).*
Acne Research: "The Superoxide Dismutase Theory". Available online as of Sep. 1, 2012 from https://acneresearch.org. pp. 1-5. (Year: 2012).*
"Foods High in Fructose, Sorbitol, Fructans and FODMAPS". Available online as of Jun. 6, 2009 from www.healthhype.com. pp. 1-7. (Year: 2009).*
"FODMAPS: How Healthy Foods Can Cause Acne". Available online as of Jul. 6, 2012 from www.acneeinstein.com. pp. 1-10. (Year: 2012).*
"The Gut-Skin Axis". Available online as of May 14, 2012 from www.acneeinstein.com. pp. 1-11. (Year: 2012).*
ISA/CN, International Search Report dated Mar. 10, 2015 in International Application No. PCT/IB2014/002312, total 4 pages.
European Patent Office, Extended Search Report dated Jun. 6, 2017 in European Patent Application No. EP14856580.7, 6 pages.
Katta, Rajani, M.D. et al., "Diet and Dermatology, The Role of Dietary Internention in Skin Disease," *J Clin Aesthet Dermatology*, vol. 7, No. 7, Jul. 16, 2014, pp. 46-51, 6 pages.
Reddit, "An apple a day brings my skin decay. It's fructose!," posted Dec. 27, 2012, https://www.reddit.com/r/acne/comments/15ip0b/an_apple_a_day_brings_my_sking_its_fructose/, downloaded Oct. 5, 2017, 4 pages.
Gibson, Peter R., M.D. et al., "Food Choice as a Key Management Strategy for Functional Gastrointestinal Symptoms," *The American Journal of Gastroenterology*, vol. 107, May 3, 2012, pp. 657-666, 10 pages.
IP Australia, Examination Report dated Mar. 29, 2019 in Australian Patent Application No. 2014338690, 7 pages.
Veith, W.B. et al., "The Association of Acne Vulgaris With Diet," *Cutis*, Aug. 2011 88(2) 84-91, 8 pages.
Gibson, P.R. et al., "Evidence-based dietary management of functional gastrointestinal symptoms: The FODMAP approach," *Journal of Gastroenterology and Hepatology*, vol. 25, No. 2, Feb. 2010, pp. 252-258, 8 pages.
Melnik, B.C. et al., "Role of insulin, insulin-like growth factor-1, hyperglycaemic food and milk consumption in the pathogenesis of acne vulgaris," *Experimental Dermatology*, Oct. 2009, vol. 18, No. 10, pp. 833-841, 10 pages.
Smith, R.N. et al., "The effect of a low glycemic load diet on acne vulgaris and the fatty acid composition of skin surface triglycerides," *Journal of Dermatological Science*, Apr. 2008, vol. 50, No. 1, pp. 41-52, 12 pages.
Danby, F. W., M.D., "Acne and milk, the diet myth, and beyond," *Journal of the American Academy of Dermatology*, vol. 52, Issue 2, Feb. 2005, pp. 360-362, 3 pages.

* cited by examiner

*Primary Examiner* — Jenna A Watts
(74) *Attorney, Agent, or Firm* — Masuvalley & Partners

(57) ABSTRACT

Disclosed herein is a method for preventing or controlling an inflammatory skin disorder (such as acne) in a subject. The method comprises administering to the subject a diet that is low in fructose, oligosaccharides and/or polyol sugars.

5 Claims, 12 Drawing Sheets

Week 0

End Week 2 of diet

End week 19  self compliant

Week 0

End Week 2 of diet

End week 21 self compliant

Week 0

End Week 5 of diet

End week 14 Self compliant

Week 0

End Week 2 of diet

DIETARY REGIME FOR TREATMENT OF ACNE

RELATED APPLICATIONS

This application claims priority to International Patent Application No. PCT/IB2014/002312, filed Oct. 27, 2014, which claims benefit of U.S. patent application Ser. No. 61/895,434 filed Oct. 25, 2013.

TECHNICAL FIELD

The present invention relates to methods for controlling or preventing acne and other inflammatory skin conditions in humans.

BACKGROUND

Acne Vulgaris is the most common skin condition in the world, and while it is generally associated with adolescence for many people acne may arrive at an older age, or persist well into adulthood. Even a significant percentage of children (4-7 years) are diagnosed with acne (1, 2).

Acne patients tend to be long-term consumers of over-the-counter (OTC) preparations, pharmaceuticals and prescribed medicines. Some patients with persistent acne have been reported to experience significant psychological injury related to the chronic and disfiguring nature of the condition (3).

For patients seeking professional help, clinical guidelines almost exclusively advise drug therapy. Research in the past thirty years has focused largely on pharmaceutical efficacy in the management of acne, achieved to varying effect with pharmacologically active compounds such as antibiotics, astringents, retinoids, herbal supplements and cleansers.

Unfortunately, many therapeutic interventions can cause serious adverse clinical events particularly in the case of oral retinoids. In addition, the overuse of topical medications, cleansers, or astringents can often worsen a patient's condition.

There is a need for new options to prevent or treat acne and other inflammatory skin conditions that resolve the significant disadvantages of existing treatments.

SUMMARY

The present invention is predicated on the clinical finding that daily consumption of foods high in fructose, oligosaccharides and/or polyol sugars can lead to acne or other inflammatory skin conditions. These clinical findings are supported by the fact that acne has been rarely observed in societies that have maintained traditional diets. This effect has been noted in communities such as the Inuit of Canada (4, 5), Okinawa islanders of Japan (6), the Ache hunter gatherers of Indonesia, and the Kitavan islanders of Papua New Guinea (6). The absence of acne in these populations clearly suggests the potential for underlying genetic or environmental factors, including diet.

In a first aspect, the present invention provides a method for assisting a subject to prevent or control an inflammatory skin disorder, the method comprising formulating a diet for the subject that is low in fructose, oligosaccharides and/or polyol sugars.

Embodiments of the first aspect of the invention may also comprise providing one or more food product(s) in accordance with the formulated diet.

In a second aspect, the present invention provides a method for assisting a subject to prevent or control an inflammatory skin disorder, the method comprising prescribing to the subject a diet that is low in fructose, oligosaccharides and/or polyol sugars.

In a third aspect, the present invention provides a method for preventing or controlling an inflammatory skin disorder in a subject, the method comprising administering to the subject a diet that is low in fructose, oligosaccharides and/or polyol sugars.

In a fourth aspect, the present invention provides a method for assisting a subject to prevent or control an inflammatory skin disorder, the method comprising: obtaining dietary information from the subject wherein said dietary information includes details of the subject's diet over a period of time; assessing the dietary information to determine the total daily content of fructose, oligosaccharides and/or polyol sugars in the subject's diet and/or determining whether one or more foodstuffs in the subject's diet is high in fructose, oligosaccharides and/or polyol sugars; and prescribing to the subject a diet that is low in fructose, oligosaccharides and/or polyol sugars.

In a fifth aspect, the present invention provides a method for selecting food products for a diet for preventing or controlling an inflammatory skin disorder, the method comprising: viewing a list of food products forming part of the diet; selecting one or more food product(s) from the list to form a daily diet list; calculating the total content of fructose, oligosaccharides and/or polyol sugars contained in the foodstuffs on the daily diet list; providing feedback to the subject as to whether the foodstuffs on the daily diet list contain a total amount of fructose, oligosaccharides and/or polyol sugars relative to a threshold daily value; and, if the amount of fructose, oligosaccharides and/or polyol sugars in the food product(s) on the daily diet list is below the threshold daily value, creating a customised daily diet for the subject.

In embodiments, the method of the fifth aspect further includes ordering at least some of the food product(s) in the customised daily diet for the subject. In embodiments, the ordering comprises communicating a food product(s) order to a merchant remote from the communication device. In embodiments, the ordering also comprises ordering the food product(s) from the food product(s) order from a production and/or storage facility and shipping the food product(s) to the subject.

Any one or more of the steps of the method of the fifth aspect may be implemented on a computer. For example, the list of food products forming part of the diet may be viewed on a display of a communication device, selection of the one or more food product(s) from the list to form a daily diet list may be carried out using a user interface of a communication device, and/or providing feedback to the subject may be carried using a user interface of a communication device.

In a sixth aspect, the present invention provides a database of information relating to the content of fructose, oligosaccharides and/or polyol sugars in a plurality of food products residing on a server computer; a user interface accessible by a subject and in communication with the database via a communication device, the user interface allowing the subject to select one or more food product(s) from the database; a processor for calculating the total content of fructose, oligosaccharides and/or polyol sugars in the selected one or more food product(s); and an output for displaying the total content of fructose, oligosaccharides and/or polyol sugars in the selected one or more food product(s) to the subject.

In a seventh aspect, the present invention provides a packaged foodstuff wherein the packaging of the foodstuff contains information or refers to information regarding the diet referred to in any one of the first to sixth aspects.

In an eighth aspect, the present invention provides a foodstuff in conjunction with information relating to the diet referred to in any one of the first to sixth aspects.

In some embodiments of these aspects of the invention, the inflammatory skin disorder is acne vulgaris.

In some embodiments of these aspects of the invention, the inflammatory skin disorder is acne rosacea.

In some embodiments of these aspects of the invention, the inflammatory skin disorder is general erythema.

In some embodiments of these aspects of the invention, the inflammatory skin disorder is poikaderma de Civette.

In some embodiments of these aspects of the invention, the inflammatory skin disorder is eczema.

BRIEF DESCRIPTION OF THE FIGURES

Embodiments of the present invention will be discussed with reference to the accompanying drawings wherein.

DETAILED DESCRIPTION

Figure 1:
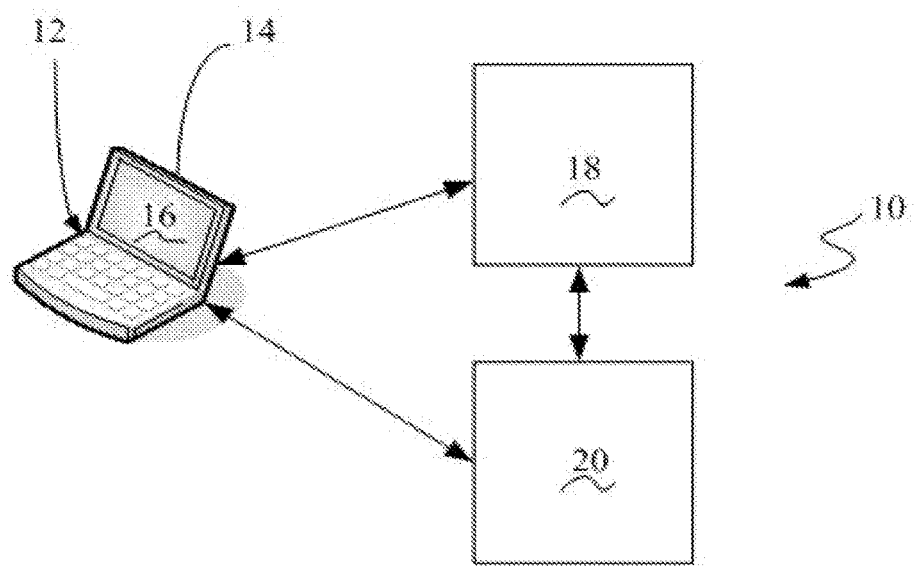
FIG. 1 is a schematic diagram of a system for creating a customised daily diet in accordance with embodiments of the invention.

The present invention, and embodiments thereof, will now be described in more detail. For ease of description, reference will be made to the treatment or prevention of acne. However, this is for illustrative purposes only and it is intended that the embodiments and aspects described can also be used in the treatment or prevention of other inflammatory skin disorders.

Before proceeding it is important to note that various terms that will be used throughout the specification have meanings that will be well understood by a skilled addressee. However, for ease of reference some of these terms will now be defined.

As used herein, the term "a diet that is low in fructose, oligosaccharides and/or polyol sugars" means a diet having a total content of fructose, oligosaccharides and/or polyol sugars that is lower than the conventional or typical diet of the subject. In embodiments, the diet that is low in fructose, oligosaccharides and/or polyol sugars contains 40 g or less per day of fructose, oligosaccharides and/or polyol sugars. However, for some subjects that amount of 40 g or less may not be low enough for the subject to prevent or control an inflammatory skin disorder. In those subjects, the individual tolerance limits in order to prevent or control an inflammatory skin disorder may need to be determined empirically. However, it is expected that the threshold level of 40 g or less will be suitable for the majority of subjects.

As used herein, the term "oligosaccharide" means a saccharide containing typically three to ten sugar units. Examples of oligosaccharides commonly found in the diet include fructans and galactans. Fructo-oligosaccharides (FOS) are found naturally in many vegetables, while inulin is a polysaccharide with a similar molecular structure to FOS but with a higher degree of polymerization.

As used herein, the term "polyol sugar" means a hydrogenated carbohydrate or sugar alcohol. Examples include xylitol, maltitol, sorbitol, erythritol, lactitol, and isomalt.

As used herein, the term "inflammatory skin disorder" is intended to include within its scope acne vulgaris, acne rosacea, general erythema, poikaderma de Civette, eczema and other conditions resulting from inflammation of the skin.

As used herein, the term "acne" is intended to include within its scope acne vulgaris and acne rosacea.

As used herein, the term "food" or "food product" means any solid or liquid material containing nutrients such as carbohydrates, proteins, and fats that are required by humans in order to obtain energy and grow.

As used herein, the term "beverage" refers to any liquid material containing water as a constituent that provides humans with the hydration necessary for normal metabolism.

As discussed, the present invention is predicated on a finding that daily consumption of foods high in fructose, oligosaccharides and/or polyol sugars can lead to inflammatory skin disorders such as acne. Recent research by others (8) has suggested an association between as low-glycemic diet with reduced sebum production and fewer acne lesions. This research did not confirm an absence of acne but fewer lesions due to a low-glycemic diet. Subsequent research (9) in 2010 found no association with acne and a low-glycemic diet. In 2006 published research (10) explored gastrointestinal symptoms resulting from the consumption of rapidly fermentable, short-chain carbohydrates (simple sugars). Based on the above evidence of the present research has shown that a low tolerance to specific simple sugars other than glucose in susceptible individuals is linked to acne development rather than a generalised consumption of high-glycemic foods.

Modern diets that include a high level of processed foods can lead to an increased consumption of specific simple sugars or their modified variants. These are present, for example, in wheat, barley or rye grains, natural sweeteners, food additives, thickeners or binding agents. The present research has shown that sensitive people who consume an excess of specific simple sugars are likely to experience a rapid gastrointestinal response that precipitates (for example) in an acne flare-up. For people with persistent acne or other inflammatory skin diseases, constant minor irritation of the small intestine due to daily consumption of a range of common foods maintains a simple sugar load higher than can be tolerated for these individuals.

Certain other food additives (for example MSG) can, during periods of lowered resistance, add to the gastrointestinal discomfort and contribute to effect of the malabsorption of specific simple sugars.

It is proposed that malabsorption in the small intestine of certain groups of short-chain carbohydrates (simple sugars) from both natural or processed sources affects the balance of gut biota. An imbalance in an individual's normal gut biota combined with the consumption of certain simple sugars, promotes the release of endotoxins that are capable of permeating the intestinal mucosa. The endotoxins migrate into the general circulatory system thereby activating an inflammatory response (11). This mechanism can lead to inflammation of skin and in susceptible individuals for example this may present as acne. This effect is pre-empted when individual tolerances for specific simple sugar load have been exceeded. Sensitivity is also exacerbated in these individuals when healthy resistance is lowered (such as hormonal fluctuations, parasite infestation or gastro-intestinal infections etc.) or by consuming certain food additives such as MSG that may irritate the small intestine. An inflammatory reaction, such as acne, is likely particularly when any of the above factors coincide.

As such, the present invention provides a method for preventing or controlling inflammatory skin diseases in a subject, the method comprising administering to the subject a diet that is low in fructose, oligosaccharides and/or polyol sugars.

A diet that is low in fructose, oligosaccharides and/or polyol sugars can be devised by determining the amounts of fructose, oligosaccharides and/or polyol sugars in food product(s) to be consumed by the subject and adjusting the diet so that the total amount of fructose, oligosaccharides and/or polyol sugars consumed by the subject is 40 g or less per day. The amounts of fructose, oligosaccharides and/or polyol sugars in food product(s) will usually be determined by determining the amounts of fructose, fructans, galactans, xylitol, maltitol, sorbitol, crythritol, lactitol, and isomalt in the food product(s).

The diet that is low in fructose, oligosaccharides and/or polyol sugars may comprise natural or commercially available foodstuffs, foodstuffs that are specifically formulated for the diet, dietary supplements, and combinations of any of these.

A suitable diet will typically include foodstuffs:
- containing complex carbohydrates in the form of grains, flakes, flours and meals from cereal grains or vegetables that are low in fructose, oligosaccharides and/or polyol sugars. Examples include flax seed, oats, corn and polished rice; and/or
- containing proteins, vitamins, minerals, carbohydrates, (simple and complex), insoluble dietary fibre, and soluble dietary fibre; and/or
- containing simple carbohydrates sourced from fruit, vegetables, grains or similar that have low levels of simple sugars particularly fructose, fructans, oligosaccharides and polyols. For example simple sugars may be selected from the group consisting of, but not limited to, rice syrup, sucrose, lactose, glucose, dextrose, stevia or other sources containing simple sugars with a higher glucose to fructose ratio.

The diet may comprise food and beverage products that are specifically formulated and manufactured for use in the diet. Suitable food and beverage products include but are not limited to: breakfast cereals, nutritional bars, snack cakes, chips, shakes, soups, soup mixes, pasta (fresh and/or dried), noodles (fresh and/or dried), ice cream, yoghurt, sorbet, beverage mixes, and beverages.

Food and beverage products that are specifically formulated and manufactured for the diet may comprise proteins, vitamins, minerals, carbohydrates, (simple and complex) and incorporate a blend of soluble and insoluble dietary fibres, and fats in appropriate amounts. The food and beverage products will normally be formulated using carbohydrates that are low in simple sugars to avoid gastro-intestinal distress that can lead to acne in susceptible individuals. The food and beverage products will also typically contain levels of fibre, protein and fats to promote fullness and ensure a healthy metabolism.

In addition to the above nutritional components, the food and beverage products may contain common ingredients such as colorants, preservatives/antioxidants, emulsifiers and flavorants and the like. Colorants, preservatives/antioxidants, emulsifiers and flavorants identified as safe for human consumption are referenced in the current edition of *Food Chemicals Codex* (*FCC*) published by the United States Pharmacopeia (USP).

Optionally, the food and beverage products may include pharmacologically active compounds known to have a role in the treatment of acne vulgaris, acne rosacea, general erythema or other inflammatory skin conditions for example poikaderma de Civette or eczema. Suitable pharmacologically active compounds include but are not limited to: prescription drugs, herbal compounds, derivatives or extracts, vitamins, minerals, fish oil, and omega-3 fatty acids.

The manufactured food and beverage products facilitate a convenient dietary regimen to prevent or control acne. To ensure a low daily consumption of simple sugars an individual can create a customised dietary regimen by replacing one or more meals, snacks or beverages with the food and beverage products that have been both nutritionally balanced and specifically formulated to prevent or control the condition.

The manufactured food and beverage products may be used singly or in combination to provide a full serving, which further enhances the subject's ability to customise their dietary regimen.

The manufactured food and beverage products may be formed by conventional techniques.

The packaging of a foodstuff suitable for use in the diet may contain information or refer to information regarding the diet. Alternatively, or in addition, the foodstuff may be provided or sold in conjunction with information relating to the diet. The information may include an indication that the foodstuff is suitable for use in the diet and/or for the control of acne. The information may also include details of the fructose, oligosaccharide and/or polyol sugar content of the product.

As discussed, I have found that consumption of the diet that is low in fructose, oligosaccharides and/or polyol sugars may lead to a reduction in the occurrence of acne in a subject or prevent occurrence of acne. Thus, the present invention also provides a method for assisting a subject to prevent or control acne, the method comprising prescribing to the subject a diet that is low in fructose, oligosaccharides and/or polyol sugars.

The methods of the invention may also comprise providing food product(s) in accordance with the formulated diet. The provided food product(s) may be packaged meals. Alternatively, or in addition, the provided food product(s) may be food beverage products specifically manufactured for the diet, as described earlier. Thus, the method may further comprise providing food product(s) for people susceptible to an inflammatory skin disorder.

Aspects of the method for preventing or controlling acne in a subject may be implemented on a computer. Thus, the present invention also provides a computer-implemented method for selecting food products for a diet for preventing or controlling an inflammatory skin disorder, the method comprising: viewing, on a display of a communication device, a list of food products forming part of the diet; selecting one or more food product(s) from the list, using a user interface of the communication device, to form a daily diet list; calculating the total content of fructose, oligosaccharides and/or polyol sugars contained in the foodstuffs on the daily diet list; providing feedback, using the user interface of the communication device, to the subject as to whether the foodstuffs on the daily diet list contain a total amount of fructose, oligosaccharides and/or polyol sugars relative to a threshold daily value; and, if the amount of fructose, oligosaccharides and/or polyol sugars in the food product(s) on the daily diet list is below the threshold daily value, creating a customised daily diet for the subject.

A simplified schematic diagram of a system 10 for creating a customised daily diet for a subject is shown in FIG. 1. The system 10 comprises a communication device 12 having a display 14, a user interface 16 displayable on the display 14, a database 18 comprising a list of food products and information relating to the content of fructose, oligosaccharides and/or polyol sugars in each of the food products, a processor 20 for calculating the total content of fructose, oligosaccharides and/or polyol sugars contained in the food product(s) on a daily diet list selected by a subject using the user interface 16 and comparing the total content of fructose, oligosaccharides and/or polyol sugars to a threshold daily value, and providing an output to the subject as to whether consumption of the food product(s) on the daily diet list are likely to prevent or control an inflammatory skin disorder in the subject.

Figure 2:
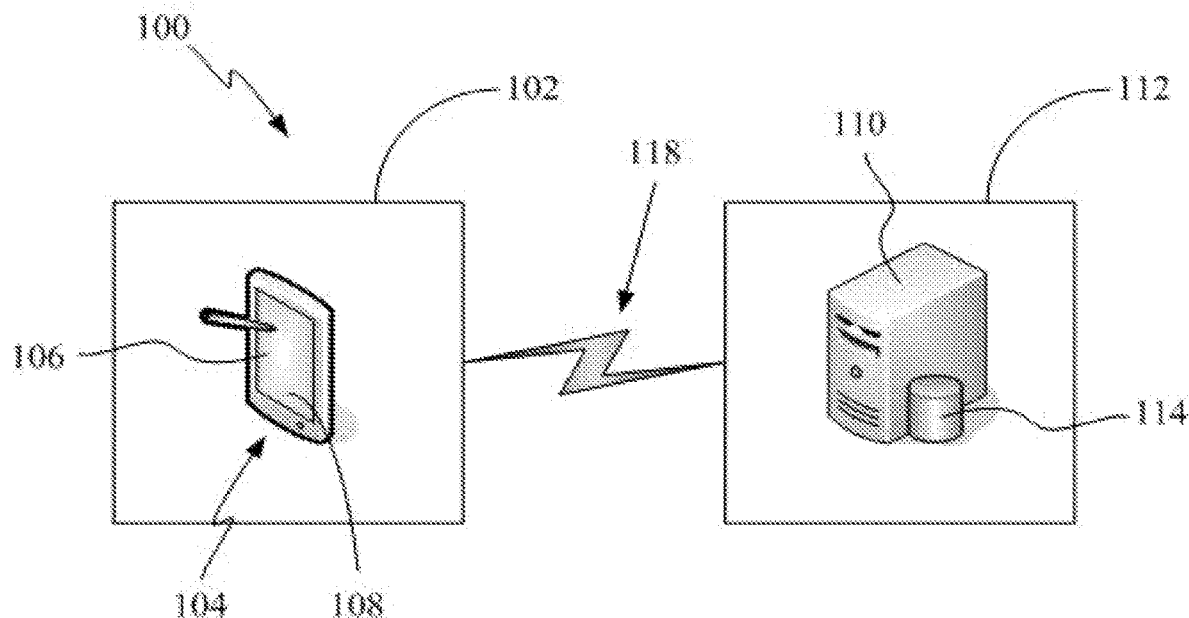
FIG. 2 is a schematic diagram of a system for creating a customised daily diet implemented across a communications network in accordance with embodiments of the invention.

In embodiments, the system 100 may be implemented across a communications network such as a local area network or the internet (FIG. 2). The system 100 comprises a subject location 102, a communication device 104 at the subject location 102, the communication device 104 comprising a display 106 and a user interface 108 displayable on the display 108. A server 110 is located at a server location 112 which is remote from the subject location 102. The server 110 comprises a database 114 comprising a list of thud products and information relating to the content of fructose, oligosaccharides and/or polyol sugars in each of the thud products and a processor 116 for calculating the total content of fructose, oligosaccharides and/or polyol sugars contained in the food product(s) on a daily diet list selected by a subject using the user interface 16 and comparing the total content of fructose, oligosaccharides and/or polyol sugars to a threshold daily value. A communications link 118 between the communication device 104 and the server 110 allows the subject to select one or more food product(s) using the user interface 108 and receive an output as w whether consumption of the food product(s) on the daily diet list are likely to prevent or control an inflammatory skin disorder in the subject.

The present invention also provides a database of information relating to the content of fructose, oligosaccharides and/or polyol sugars in a plurality of food products residing on a server computer; a user interface accessible by a subject and in communication with the database via a communication device, the user interface allowing the subject to select one or more food product(s) from the database; a processor for calculating the total content of fructose, oligosaccharides and/or polyol sugars in the selected one or more food product(s); and an output for displaying the total content of fructose, oligosaccharides and/or polyol sugars in the selected one or more food product(s) to the subject.

In embodiments, the methods include ordering at least some of the food product(s) in the customised daily diet for the subject. In embodiments, the ordering comprises communicating the food product(s) order to a merchant remote from the communication device. In embodiments, the ordering also comprises ordering the food product(s) from the food product(s) order from a production facility; producing the food product(s); and shipping the food product(s) to the subject.

EXAMPLES

Elimination Diet for the Control of Acne

A study was conducted to establish the effect of a dietary intervention on subjects with Acne Vulgaris for two week intervals over three sessions in February, May and September 2014 in Vientiane Lao PDR. The typical Lao diet generally consists of little to no wheat flour, breads, pasta or other wheat based products and is therefore an ideal cohort to maximise compliance for this dietary intervention.

Independent pre- and post-assessment of subjects for the severity a acne was achieved with the help of the National Centre of Dermatology located in Vientiane Lao PDR. A Lao speaking assistant assisted with translation as needed during the dietary interventions.

Subjects

Inclusion criteria: Adult males or females with persistent moderate to severe facial acne.

Exclusion criteria: Current use of isotretinoin or antibiotics, parasite infestation, excessive alcohol intake, illicit drug use, physical or mental illness, diabetes, diagnosed food allergy or intolerance, veganism or vegetarianism. Practical exclusion criteria included impending school or university examinations, or scheduled work or family commitments outside of Vientiane during the intervention period.

It was anticipated that most subjects would deviate to some extent from the dietary intervention. For this reason it was critical to select subjects who were most likely to remain compliant with the diet and not supplement with other foods. To reduce the risk of non-compliance the following parameters were followed:

- Although teenagers typically form the largest group of people with acne, adult subjects were chosen as they were more likely to comply with the dietary restrictions within the timeframe.
- Two weeks was determined to be an adequate timeframe to alter intestinal microbiota and provide an opportunity for existing lesions to begin healing. Subjects supplied photos at random intervals for several months once the formal intervention concluded and they had established self-compliance to exclude or reduce specific simple sugars from their normal diet.
- Subjects were resident in Vientiane and were recruited using Social Media request in Lao language (Facebook) a well as via word-of-mouth.
- Subjects were excluded from the study if food diaries were not completed or if subjects failed to collect prepared food on schedule every two days.

Study Protocol

Subjects participated in the study at no cost. Agreement with subjects included the collection and analysis of stool samples as well as the provision of photographs pre and post intervention. Subjects were interviewed (in English and Lao) and an overview of the intervention was described but without specific details of the diet, to avoid subjects modifying current dietary practices before completing their pre-diet diary.

Subjects supplied a diet diary of all food, drinks and or medicines consumed for 5-7 days prior to the intervention to establish what in their regular foods may have high levels of specific simple sugars.

Stool tests prior to the dietary intervention were analyzed by a local Vientiane clinic for parasite infection. Helminthic treatment was supplied at no cost to subjects prior to the intervention.

Subjects maintained their current personal cleansing regime. Topical treatments/cosmetics if used by subjects were not excluded during the intervention.

Subjects were asked to only consume prepared foods and agree to exclude any non-prescribed medicines, vitamins or supplements.

Subjects were assessed at the dermatology hospital prior to the intervention.

Subjects were counselled (in English and Lao) prior to the intervention including identifying the source and types of simples sugars described in their diet diaries that may be contributing to their acne.

Every two days a generous amount of prepared meals, drinks and snacks of simple Lao/Western cuisine low in specific simple sugars were collected by individual subjects.

Prior to collection all prepared foods were photographed.

Food diaries were completed by subjects on a daily basis and collected at the end of the intervention and included food items not supplied as part of the intervention.

After the intervention, subjects were taken to a local fresh vegetable market where they were able to photograph foods that were low and high in specific simple sugars to help them with continued self-compliance.

At baseline and followed up at two weeks, the severity of facial acne was assessed for each subject in person by the same dermatologists (Dr Buddha and Dr Ammala together, or Dr. Ammala alone) from the National Dermatology Centre and photographs were taken.

No blood or other tests were taken as part of this intervention.

A Lao-English translator was employed to translate from Lao to English the before-after dermatology reports for each subject.

Subjects were coached throughout the intervention period, and followed up where needed at monthly intervals during self-compliance.

Food was prepared for 4-5 subjects per session for a two week period. Foods included were meat, poultry, fish, eggs, home-made soups, and a wide selection vegetables, rice and rice noodles. A live yoghurt preparation was supplied.

Processed foods including most condiments were excluded due to the usual ingredients containing Monosodium Glutamate (MSG) and/or the specific simple sugars excluded as part of this intervention. Home made chili sauces, live yoghurt, low-sugar commercial mayonnaise were included for variety.

Subjects supplied their own cooked rice to supplement each meal.

Results and Discussion

Ten subjects participated over three sessions for a period of two weeks per session—in February, May and September 2014 in Vientiane, Lao PDR.

Two initial subjects in February 2014 were not assessed by staff from the National Dermatology Hospital, however photos and diet diaries were recorded for this period.

The same dermatologist from the National Dermatology Hospital assessed all 8 subjects pre- and two weeks post-diet in May and September. All subjects maintained a diet diary throughout the diet intervention.

Food both fresh and cooked was supplied to subjects every two days with total simple sugars (fructose, oligo-saccharides, polyols) averaging less than 40 g per day

- All foods or beverages high in fructose, oligo-saccharides, or polyols were excluded
- Processed foods were generally not supplied apart from small amounts of fish sauce of soy sauce used as flavouring
- Generally meals consisted of meat, fish, poultry, salad, vegetable, herbs, chili, fermented fish paste, nuts, dairy, oatmeal, rice, popcorn, soda water, rice noodles, live yoghurt.
- Recommended daily allowance of fibre (15-20 g) was sufficient via the natural foods provided
- Cooked polished rice was supplied as needed by each subject
- Prepared foods were photographed prior to each pickup Independent reports from the Lao National Dermatology Hospital were provided for each subject, each of which was examined pre- and post-diet. Initial examination occurred up to five days before dietary intervention commenced. Final examination occurred on last day of diet. Subjects were self-compliant after first two weeks. Reports provided below were originally written in Lao language and are supplied with the English translation.

Additional notes by the applicant are included with each report where background information related to the dietary intervention is needed for individual subjects.

Subsequent photos provided in the weeks following the two-week intervention are when subjects are self-compliant to stay with the low simple sugar regime.

Subject 1 Report

Female, age 24

Diagnosis: Acne, normal/moderate

Got acne 2 weeks ago. Acne type: whiteheads, has a group of pustules (pimples that have pus) located at lower side of both cheeks, itchy a bit. So far, have been applying skin cream, Betnevert-N; feel more itchy when applying.

Note: Stool exam confirmed strongyloides parasite and treatment was provided prior to commencing diet. Subject used a paste of baking soda and other irritants on acne throughout diet period that has inflamed her skin, although it is gradually improving. Menstrual period occurred during diet phase.

Report after 23 days: Diagnosis: Acne. Compared to before treatment, there are some redness and still some pustules occurred at the lower cheek but no sign of itchiness. As for old acne zone mostly has seen a reduction or disappearance, but a few new pimples revealed at new zones.

Figure 3:
FIG. 3 shows photographs of subject 1 at weeks 0, 2, 4 and 5.

Photographs of the subject at weeks 0, 2, 4 and 5 are provided in FIG. 3.

Subject 2 Report

Male, age 27.

Diagnosis: Acne

Affected by acne more than 1 year. Used to take regular tablets of Doxycycline Erythromycin, Declofemate Fexet and some acne skin gel from Hospital 103.

Actual examination: Acne scars and few group of pustules (pimples with pus) at both sides of the cheek, with presence of both whitehead and blackhead pimples. Few small whitehead pimples at the chin.

Note: Parasite infection confirmed by stool test and subject was treated for liver fluke prior to commencing diet. Subject had concluded 2 months treatment with Doxycycline prior to commencing diet with only modest improvement (self-reported).

Report after 15 days: Diagnosis: Acne. Compared to before treatment, there is some improvement and looking better. Now, remains minor pimples about 2-3 buttons appeared at the right cheek, face is not so red; some imprint scars after buttons disappeared, only 1 button at the right cheek and no new button.

Figure 4:
FIG. 4 shows photographs of subject 2 at weeks 0, 2, 4 and 5.

Photographs of the subject at weeks 0, 2, 4 and 5 are provided in FIG. 4.

Subject 3 Report

Female, age 29.

Diagnosis: normal/moderate acne.

Has been affected by acne more than 20 years and was continuously suffered from then. Acne is papules, whiteheads, acne scars, a few pustules at both side of the cheeks, chin, under the chin. Used to apply with skin cream Corsine, and have been treated for acne Nitikone clinic.

Note: Subject was confirmed free from parasites by stool exam prior to diet. Menstrual period occurred during diet phase. Subject later confirmed acne duration has been for 15 years not 20 as stated in above report.

Report after 13 days: Diagnosis: Acne. In comparison to before treatment, there are some improvements. Examination: There are still a few papules; whitehead pimple scars has decreased. Old pustules have gone down however one new cyst is showing up at the left cheek. Overall, no sign of the new pimples.

Figure 5:
FIG. 5 shows photographs of subject 3 at weeks 0, 2, 4 and 5.

Photographs of the subject at weeks 0, 2, 4 and 5 are provided in FIG. 5.

Subject 4 Report

Female, age 23.

Diagnosis: normal/moderate acne.

Affected by acne for over 10 years. Used to take Vit C tablets, Japanese skin cream. Used facial soap especially for acne and took Japanese supplement tablets.

Actual examination: Some papules, whiteheads, acne scar, some pustules on the forehead, chin, both side of the cheeks.

Ascaris parasite confirmed by stool exam. Subject treated prior to diet. Menstrual period occurred during diet phase.

Report after 12 days: Diagnosis: Acne. Compared to the before treatment, it looks much better. Actual examination: Still has some whitehead acne and remains of pit scar acne at both sides of the cheeks, forehead but no pustule, and no new pimples.

Figure 6:
FIG. 6 shows photographs of subject 4 at weeks 0, 2, 4 and 5.

Photographs of the subject at weeks 0, 2, 4 and 5 are provided in FIG. 6.

Subject 5 Report

Female, age 28.

Diagnosis: moderate acne.

Affected by acne for 3 years. Used to be treated by injection morning and evening for 5 days (don't know the name of drug) in 2012; after stopping injection for 3 months, acne came back again. Used to suffer from gastritis.

Present illness: Multiple pit scars on both cheeks and a few papules and pustules.

Note: Stool exam prior to diet found Ascaris and liver fluke. Treated for ascaris parasite prior to diet but treated for liver fluke end of week 1. Follow up stool test for parasite repeated day 14 with clear result. Menstrual period, occurred during diet phase. Subject consumed vitamin supplement containing fructose during Week 1 of diet.

Report after 19 days: Diagnosis: Moderate acne. Have a few red dots, pustules present at both side of the cheeks, chin and neck. Conclusion: when comparing to the last 2 weeks, now it looks better and improved a lot.

Figure 7:
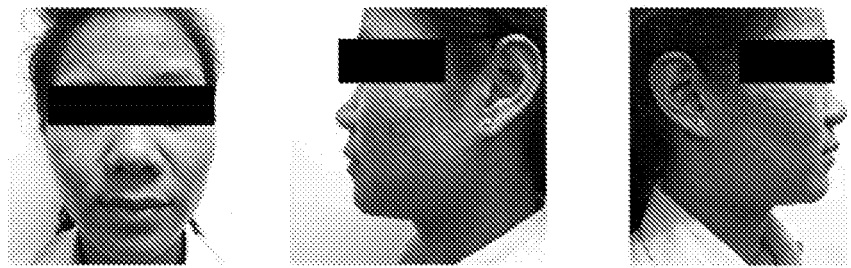
FIG. 7 shows photographs of subject 5 at weeks 0, 2 and 19.
Figure 7:
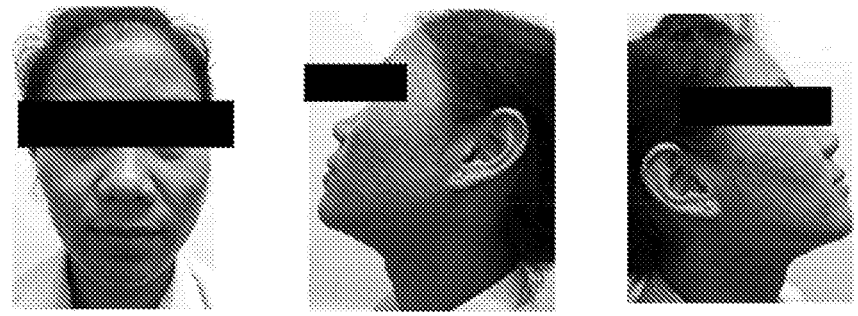
Figure 7:
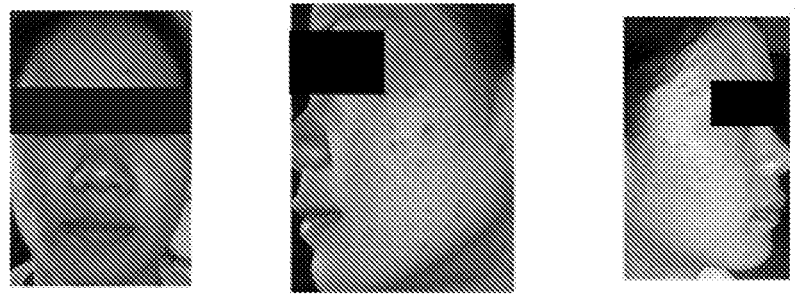

Photographs of the subject at weeks 0, 2 and 19 are provided in FIG. 7.

Subject 6 Report

Female, age 21,

Diagnosis: moderate acne.

Have had acne for more than 4 years. Acne has been slowly increasing, however, more pimples during menstruation period. Used to be treated at Nitikon clinic for more than 1 year, acne seems to disappear during the treatment period but it returned when ceased treatment.

Present illness: Multiple pit scars, a few papules, pustules and whitehead came out on both checks and forehead.

Note: Stool test confirmed ascaris parasite. Subject treated before commencing diet. Menstrual period occurred during 2 week diet phase. Subject had resolved acne by Week 4. Recurrence by Week 19 after consumption of vitamin supplements containing fructose. Subject provided images for Weeks 4 and 19.

Report after 19 days: Diagnosis: Moderate acne. Still remains a few pustules in some areas but pustules are not large and some pit scars acne remain. Conclusion: compared to the last 2 weeks, it looks better.

Figure 8:
FIG. 8 shows photographs of subject 6 at weeks 0, 2, 4 and 19.

Photographs of the subject at weeks 0, 2, 4 and 19 are provided in FIG. 8.

Subject 7 Report

Male, age 32.

Diagnosis: Pit scar, acne+a few pimples.

Affected by acne since the age of 15, moderately and continuously. Have used pills, injection, laser treatment and removing pimples head, most recently have been treated at Wutisack clinic for 3-4 mouths. Present: Pit scars acne with a few pimples.

Note: Subject had been treated with Isotretinoin 5 years earlier. Mostly scarring on jawline. Subject was confirmed clear from parasites by stool exam prior to start of diet.

Report after 19 days: Diagnosis: Acne, grade 1+scar acne. Present: have few pimples with pus (pustules) and pit scars. Conclusion: when compared to the last 2 weeks there is much improvement.

Figure 9:
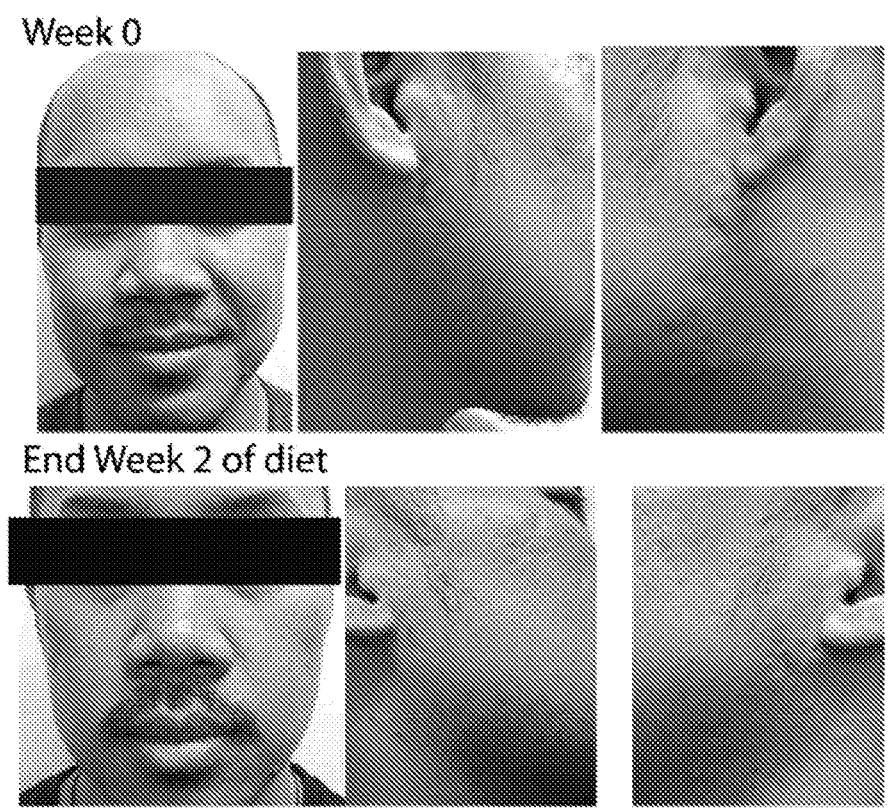
FIG. 9 shows photographs of subject 7 at weeks 0 and 2.

Photographs of the subject at weeks 0 and 2 are provided in FIG. 9.

Subject 8 Report

Female, age 25.

Diagnosis: Acne, grade 1.

Had acne 3 years ago, continuously. Currently: shown groups of acne scars and few whiteheads pimples and pustules on the face. Has been treated at Wutisack clinic for 3 months.

Note: Subject had been prescribed Isotretinoin 12 months earlier (Wutisack Clinic). Stool test confirmed liver fluke.

Subject was treated for parasite prior to commencing diet. Menstrual period occurred during diet phase.

Report after 19 days: Diagnosis: Acne, grade 1. Still has a few pustules on the left cheek, meanwhile at the right cheek and at the chin, remains of pit scars after pimples' disappearance. Conclusion: compared to the last 2 weeks, it looks much better.

Figure 10:
FIG. 10 shows photographs of subject 8 at weeks 0, 2 and 21.
Figure 10:
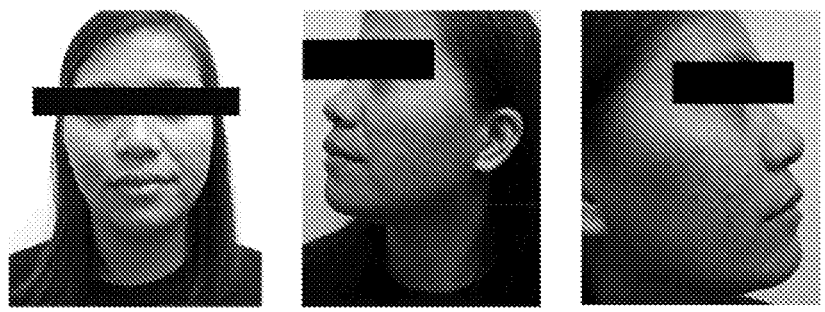
Figure 10:

Photographs of the subject: at weeks 0, 2 and 21 are provided in FIG. 10.

Subject 9 Report

Female, age 30.

Diagnosis: Moderate Acne. Still have some red papules shown under the chin.

Note: Subject as first to complete the diet in February-March 2014. Subject received prepared foods for 5 weeks due to late detection of parasite infection. Stool analysis end week 1 confirmed Hymenolepis Nana (Dwarf Tapeworm). Analysis end week 3 confirmed Taenia Tapeworm. Treated for parasites beginning week 2 and week 4. Because of parasite infestation, food was supplied for 5 weeks.

Note: Subject did not attend an examination prior to commencing the diet, but received an examination after 9 weeks of self-compliance. During examination dermatologist was shown photographs of the subject over a total of 14 weeks for comparison.

Figure 11:
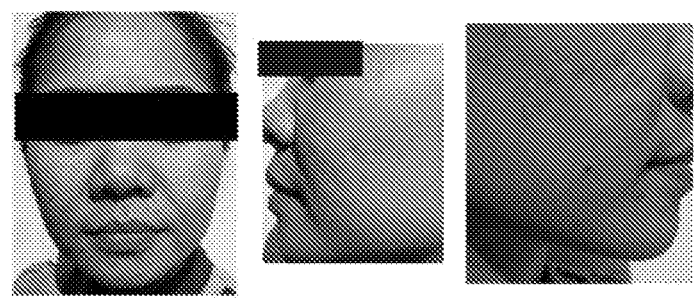
FIG. 11 shows photographs of subject 9 at weeks 0, 5 and 14.
Figure 11:
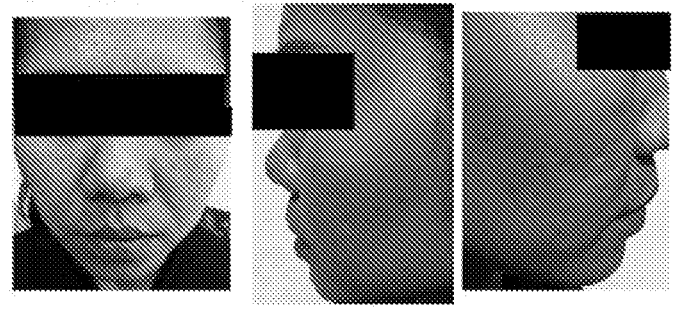
Figure 11:
Figure 12:
FIG. 12 shows photographs of subject 9 at weeks 0, 1, 2, 3, 5 and 14.

Photographs of the subject at weeks 0, 5 and 14 are provided in FIG. 11. Photographs of the subject at weeks 0, 1, 2, 3, 5 and 14 are also provided in FIG. 12.

Subject 10 Report

Note: 31 YO Subject participated in diet for 2 weeks in February-2014.

Note: Mostly acne scarring. Subject was not examined pre-post diet at the Lao National Dermatology hospital. Photos at end of Week 2 show subject with conjunctivitis.

Figure 13:
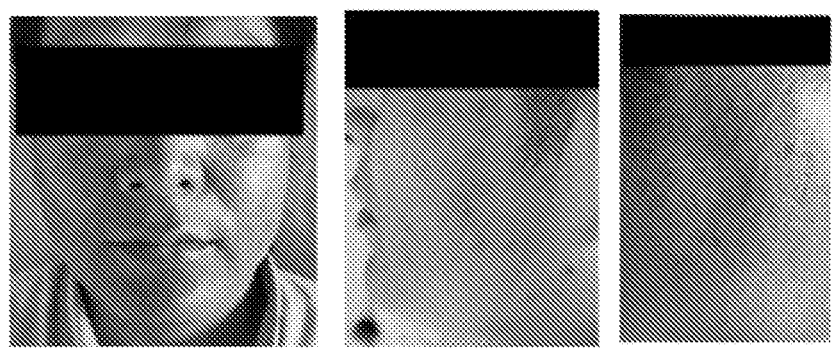
FIG. 13 shows photographs of subject 11 at weeks 0 and 2.
Figure 13:

Photographs of the subject at weeks 0 and 2 are provided in FIG. 13.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The reference to any prior art in this specification is not, and should not be taken as, an acknowledgement of any form of suggestion that such prior art forms part of the common general knowledge.

REFERENCES

1. Kilkenny M, Merlin K, Plunkett A, et al: The prevalence of common skin conditions in Australian school students: acne vulgaris. Br J Dermatol 139: 840-845, 1998.
2. Lello J, Pearl A, Arroll B, et al: Prevalence of acne vulgaris in Auckland senior high school students. N Z Med J 108: 287-289, 1995.
3. Katzman and Logan Acne vulgaris: Nutritional factors may be influencing psychological sequelae - Medical Hypotheses (2007) 69, 1080-1084
4. Hansman FS: Biochemistry in relation to the aetiology of acne vulgaris. Aust J Dermatol 1: 120-124, 1951.

REFERENCES -continued

5. Schaefer O: When the Eskimo comes to town. Nutr Today 6: 8-16, 1971.
6. Steiner PE: Necropsies on Okinawans. Anatomic and pathologic observations. Arch Pathol 42: 359-380, 1946
7. Cordain L, Lindeberg S, Hurtado M, et al: Acne vulgaris: a disease of Western civilization. Arch Dermatol 138: 1584-1590, 2002
8. Smith, R et al. The effect of a low glycemic load diet on acne vulgaris and the fatty acid composition of skin surface triglycerides. Journal of Dermatological Science (2008) 50, 41-52
9. Reynolds et al: Effect of Glycemic Index of Carbohydrates on Acne Vulgaris: Nutrients 2010 2, 1060-1072
10. Shepherd SJ, Gibson PR, Fructose malabsorption and symptoms of irritable bowel syndrome: guidelines for effective dietary management. J. Am. Diet. Assoc. 2006; 106: 1631-9.
11. Tremellen K, Pearce K Dybiosis of Gut Mibcrobiota (DGMA) - A novel theory for the development of Polycystic Ovarian Syndrome: Medical Hypotheses 79(2012) 104-112.

The invention claimed is:

1. A method for preventing or controlling acne vulgaris in a subject, the method comprising administering to the subject a diet that has a cumulative daily total of 40 g or less of fructose, oligosaccharides and polyol sugars.

2. The method of claim 1, the method further comprising: obtaining dietary information from the subject wherein said dietary information includes details of the subject's diet over a period of time; assessing the dietary information to determine the total daily content of fructose, oligosaccharides and polyol sugars in the subject's diet and/or determining whether one or more foodstuffs in the subject's diet is high in fructose, oligosaccharides and polyol sugars; prescribing to the subject the diet that has a cumulative daily total of 40 g or less of fructose, oligosaccharides and polyol sugars; and administering to the subject the diet that has a cumulative daily total of 40 g or less of fructose, oligosaccharides and polyol sugars.

3. A method for treating or preventing acne vulgaris, the method comprising: viewing a list of food products forming part of a diet; selecting one or more food product(s) from the list to form a daily diet list; calculating the total content of fructose, oligosaccharides and polyol sugars contained in the foodstuffs on the daily diet list; providing feedback to a subject as to whether the foodstuffs on the daily diet list contain a total amount of fructose, oligosaccharides and polyol sugars of 40 g or less per day; and, if the amount of fructose, oligosaccharides and polyol sugars in the food product(s) on the daily diet list is below 40 g or less per day, creating a customised daily diet for the subject; and administering to the subject the customised daily diet.

4. The method of claim 3, further comprising ordering at least some of the food product(s) in the customised daily diet for the subject.

5. The method of claim 3, wherein the list of food products forming part of the diet are contained on a database of information relating to the content of fructose, oligosaccharides and polyol sugars in the food products; the database residing on a server computer; a user interface accessible by a subject and in communication with the database via a communication device, the user interface allowing the subject to select one or more food product(s) from the database; a processor for calculating the total content of fructose, oligosaccharides and polyol sugars in the selected one or more food product(s); and an output for displaying the total content of fructose, oligosaccharides and polyol sugars in the selected one or more food product(s) to the subject.

* * * * *